United States Patent [19]

Wood et al.

[11] 4,444,335
[45] Apr. 24, 1984

[54] DELIVERY OF ADJUSTABLE QUANTITIES OF MATERIALS

[75] Inventors: William E. Wood, Hudson, Mass.; Roy A. Rosen, Woodstock, Conn.

[73] Assignee: Merck & Co., Inc., Rahway, N.J.

[21] Appl. No.: 301,671

[22] Filed: Sep. 14, 1981

[51] Int. Cl.³ .......................... G01F 11/02; B67D 5/02
[52] U.S. Cl. ....................................... 222/43; 222/309; 604/208
[58] Field of Search .................. 222/43, 45, 47, 49, 222/309; 73/429; 604/208, 209, 210, 220, 201, 224

[56] References Cited

U.S. PATENT DOCUMENTS

| | | | |
|---|---|---|---|
| 1,569,457 | 1/1926 | Carstens | 604/210 X |
| 2,128,254 | 8/1938 | Kile | 222/309 |
| 2,523,850 | 10/1950 | Steinberg | 604/209 |
| 2,695,023 | 11/1954 | Brown | 604/210 |
| 3,110,310 | 11/1963 | Cislak | 604/209 |
| 3,248,950 | 5/1966 | Pursell | 604/209 |
| 3,831,602 | 8/1974 | Broadwin | 222/309 X |
| 3,905,521 | 9/1975 | Mead et al. | 604/208 X |
| 4,006,849 | 2/1977 | Van Vroenhoven | 222/309 |
| 4,074,831 | 2/1978 | Roach | 222/43 |
| 4,141,251 | 2/1979 | Oshikubo | 222/309 X |

Primary Examiner—Joseph J. Rolla
Assistant Examiner—Michael S. Huppert
Attorney, Agent, or Firm—Thomas E. Arther; Mario A. Monaco

[57] ABSTRACT

A delivery device and method making use of a plunger which can be controllable reciprocated within a housing to regulate the amount of material expelled from the housing. The plunger includes an adjustable stop collar which can be adjustably positioned, preferably by depressing the sides of the collar. In addition, a piston within the housing is sealably releasable from the plunger.

1 Claim, 10 Drawing Figures

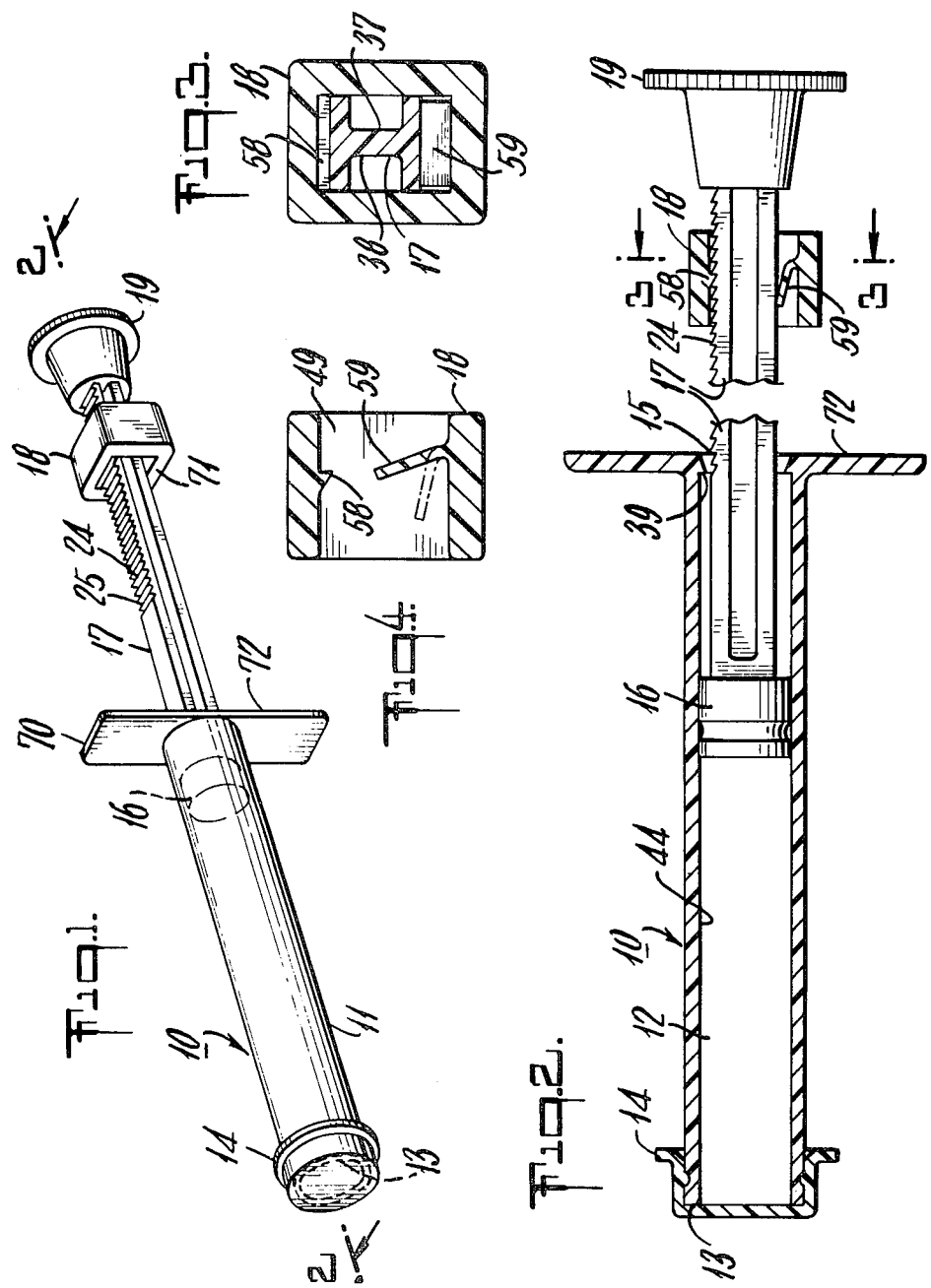

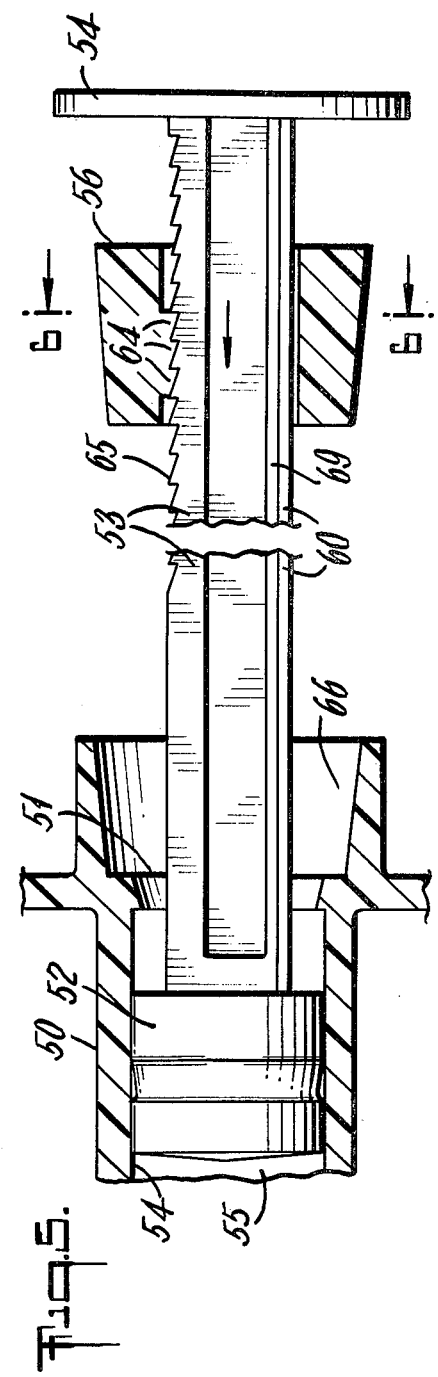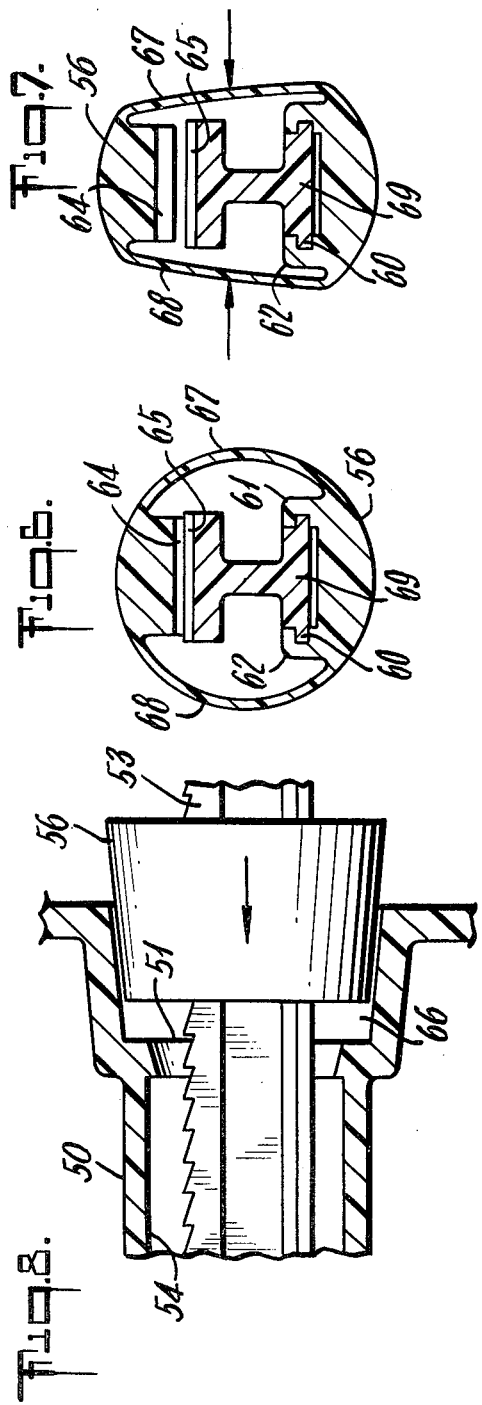

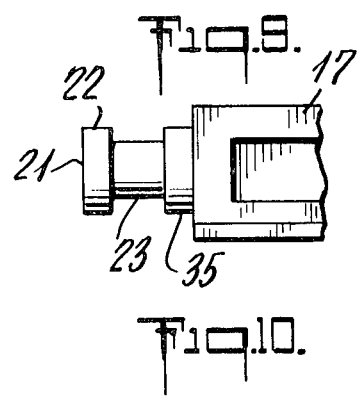
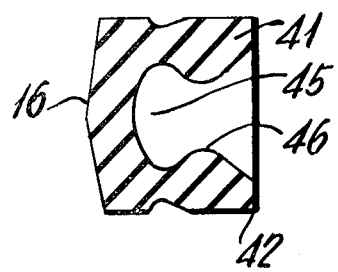

DELIVERY OF ADJUSTABLE QUANTITIES OF MATERIALS

BACKGROUND OF THE INVENTION

This invention relates to the delivery of adjustable quantities of material, and, more particularly, to the dispensing of measured amounts of material from a dispenser.

The dispensing of measured amounts of materials are required in many situations. One such situation is the dispensing of incremental dosages of gels or paste materials. The latter are often used as medicaments.

The typical dispensation of gel or paste medicaments has made use of devices which are difficult to adjust and, once adjusted, easily disturbed from their preset adjustment.

Such is the case, for example, with the commonly used, continuously threaded plunger. This device has a retaining ring that is threaded on the plunger and rotated to a desired position. The threading of the retaining ring is often a slow and cumbersome procedure. In addition, once positioned it is a relatively simple matter to disturb the preset position. As a result, the accuracy and utility of this kind of device is far from satisfactory.

Accordingly, it is an object of the invention to facilitate the delivery of adjustable quantities of materials. A related object is to facilitate the dispensing of paste and gel materials, for example medicaments.

Another object of the invention is to achieve precision in the dispensing of materials. A related object is to achieve precision in the dispensing of gel and paste medicaments.

Still another object of the invention is to achieve control over the dispensing of materials in a simple and efficient way. A related object is to adjust the dispensed amount of materials in rapid fashion.

A still further object of the invention is to overcome the disadvantages associated with dispensers making use of continuously threaded plungers. A related object is to increase the ease of adjustment over that afforded by continuously threaded plungers. Still another related object is to achieve security in the setting established for the dispensing of material, particularly a medicament.

SUMMARY OF THE INVENTION

In accomplishing the foregoing and related objects, the invention provides a delivery system in which a housing with an outlet for material to be delivered receives a reciprocating plunger, and the reciprocation of the plunger is regulated to control the amount of material delivered from the outlet.

In accordance with one aspect of the invention, means are provided for sealing the inlet of the housing. The sealing is desirably achieved by a member, such as a piston which is detachable from the plunger. For that purpose, the member advantageously includes a central opening with convex walls for releasably engaging the plunger. Similarly, the plunger is proportioned to receive the releasable member. This can be done by providing spaced apart prongs at the end of the plunger to receive the convex walls of the member. Illustratively, the prongs are cylindrical and separated from one another by a shoulder which is narrower than the prongs and positioned along the common axis of the prongs.

In accordance with another aspect of the invention, the sealing member includes concave outer walls which combine with convex inner walls to form a seal when the plunger is in engagement with the convex walls, as well as when the plunger is withdrawn from the housing.

In accordance with still another aspect of the invention, the extent of reciprocation of the plunger in the housing is controlled by a stop on a portion of the plunger exterior to the housing. The stop is adjustably positioned on the housing, and is desirably in the form of a collar which surrounds the plunger. The collar, advantageously has compressible side portions for adjusting the position of the collar on the plunger to control the extent of reciprocation. The collar may also include a flexible inner member which engages the plunger to assist in fixing the adjustable position of the collar.

In accordance with yet another aspect of the invention, the plunger includes a discrete series of depressions for adjusting the position of the stop. The depressions can be in the form of discrete grooves which are transverse to the principal axis of the plunger. The stop may also include one or more interior projections for engaging the grooves. In particular, it is desirable for each projection to be contoured to mesh with the grooves. A further projection, in the form of a flexible member, may also engage additional grooves of the plunger. The flexible member has a spring-like effect and is advantageously formed integrally with the collar which can be of plastic material.

In accordance with a further aspect of the invention, the plunger can have an I-beam cross section and it can bear graduations to indicate the collection between the extent of reciprocation and the amount of material being expelled from the housing. The grooves on the plunger can be in the form of ratchet teeth forming an angle with the axis of the plunger ranging up to 90°. When the back face of each tooth is at 90°, inadvertent backward movement of the stop collar is prevented. The portion of each tooth forward of the back surface is desirably in the form of an inclined ramp. This facilitates forward adjustment of the collar without interfering with the desired stopping action. The housing may also include a distal recess which is configured according to the profile of the collar in order to promote the desired precision of the measured dispensing of prescribed quantities of materials by the engagement of the stop collar within the housing.

DESCRIPTION OF THE DRAWINGS

Other aspects of the invention will become apparent after considering several illustrative embodiments, taken in conjunction with the drawings, in which:

FIG. 1 is a perspective view of a delivery device in accordance with the invention;

FIG. 2 is a cross-sectional view of the delivery device of FIG. 1 taken along the axis 2—2;

FIG. 3 is a cross-sectional view of a stop member on the plunger of the delivery device of FIG. 2, taken along the axis 3—3;

FIG. 4 is a cross-sectional view of the stop member of FIG. 3, shown removed from its associated plunger;

FIG. 5 is a partial cross-sectional view of an alternative embodiment of a delivery device in accordance with the invention;

FIG. 6 is a cross-sectional view of the stop member of FIG. 5 taken along the axis 6—6;

FIG. 7 is a cross-sectional view corresponding to FIG. 6 showing the side wall of the stop member being depressed in order to control the positioning of the stop member along the associated plunger;

FIG. 8 is a partial sectional view showing the relation between the inlet of the housing for the delivery device of FIG. 5 and the stop member on the plunger;

FIG. 9 is partial view showing the end of the plunger used in a delivery device according to the invention and its associated hub for a piston within the device; and FIG. 10 is a sectional view of an illustrative piston for engagement by the hub of FIG. 9.

DETAILED DESCRIPTION OF THE INVENTION

With reference to the drawings, FIG. 1 shows delivery device 10 in accordance with the invention including a housing 11 and a reciprocating plunger 17. The housing 11 has an inlet 15 for receiving the plunger 17. The opposite end of the housing 11 includes an outlet opening 13 shown covered by a protective cap 14. Within the housing 11 is a piston 16 which is engagable and disengagable with respect to the plunger 17 in a manner specifically described below.

The plunger 17 additionally includes a stop member or collar 18 which is positionally adjustable along the plunger with respect to a set of grooves 24,25. The exterior end of the plunger includes a boss or pommel 19 for the application of manual pressure to the plunger 17 in order to force it into the housing 11 and subsequently withdraw it from the housing 11. The housing 11 illustratively includes an end flange 70 to facilitate gripping and positioning of the device 10 during use. The plunger 17 is then moved forward using the pommel 19 until a limiting face 71 of the stop member 18 engages a mating face 72 of the flange 70.

The housing 11 of FIG. 1 is illustratively in the form of a cylindrical barrel, but any convenient cross section may be employed. The piston 16 is configured according to the cross section of the barrel. For the cylindrical barrel of FIG. 1, the piston 16 is shown with a circular cross section.

In the cross-sectional view of FIG. 2, the piston 16 is shown in coupling engagement with the plunger 17. The manner in which the piston 16 can be disengaged from the plunger 17 is described below. In any event, when the plunger 17 is withdrawn towards the flange 70, after there has been engagement with the stop surface 72 of the flange by the collar 18, it ultimately engages a rim 39 which prevents the piston 16 from being withdrawn from the housing 11. In addition, the periphery of the piston 16 forms a seal with the rim 39 so that any material within the housing 11, for example, a medicament 12, will not leak from the inlet 15, but can only be expelled from the outlet 13 after the protective cap is removed. The seal provided by the piston 16, both when the piston is at an intermediate position within the housing 11 as illustrated in FIG. 2 and when the piston is at the distal end of the housing 11, as the plunger is being withdrawn, not only prevents leakage but also avoids inadvertent contamination.

The control over the extent of expulsion of the medicament 12 by the reciprocating action of the plunger 17, when the cap 14 is removed, is also illustrated in FIG. 2. For that purpose the plunger 17 is in the form of a rod with a set 24,25 of depressions which advantageously are transverse grooves with respect to the longitudinal axis of the plunger 17. In particular the grooves 24,25 are shown parallel to one another and form an angle in the range from about 30° to 90° with respect to the longitudinal axis of the rod 17. As illustrated in FIG. 2 the angle of the grooves is 90° at the back of each groove, and the remainder of the groove is formed by an inclined ramp having an angle in the range between 15° and 45°, preferably 30°. The desired control is achieved by adjusting the collar 18 with respect to the grooves 24,25.

As seen in FIG. 2, considered with FIGS. 3 and 4, the collar 18 includes a flexible internal pawl 59 which bears against a lower surface of the rod 17. The collar 18 also includes an upper internal projection 58 which engages one of the grooves 24,25. Because of the flexible member 59 the projection 58 engages a selected one of the grooves 24,25. When it is desired to adjust the collar, and thus the extent to which the plunger can be moved into the housing 11, the collar 18 is elevated, compressing the member 59, and elevating the projection 58 above the level of the grooves 24,25. The collar can be moved towards the stop surface 72 of the housing 11 or towards the pommel 19 at the distal end of the rod 17.

It is to be noted that the rod 17 includes indented sides 37 and 38 which can be marked by graduations that indicate the quantity of material delivered at the outlet 13 when the collar is at a particular setting and the rod has been pushed into the housing to the position where the stop face 71 of the collar 18 engages the stop face 72 of the flange 70. As illustrated in FIG. 4, the flexible member 59 is spring-like in its effect and, when withdrawn from the rod 17, is in a comparatively elevated position with respect to the normal operational position shown in phantom in FIG. 4. It will be appreciated that the surface of the rod 17 opposite the surface containing the grooves 24,25 may also include depressions (not shown) for receiving the tip of the member 59 and further fix the position of the collar 18 at a specified location. The collar 18 includes an opening 49 which provides sufficient space to clear the grooves 24,25 when the collar is elevated and the flexible member 59 is compressed. The collar 18 is advantageously a plastic material and the member 59 accordingly forms a plastic, flexible pawl. The particular internal projection 58 is shown with a profile that meshes with the transverse grooves 24,25, so that a ratcheting effect is provided and the collar 18 can be slid towards the stop surface 72, but is firmly seated against any rearward motion.

In using the delivery device 10, a suitable material such as a medicament 12, is loaded into the housing 11 after the cap 14 has been removed and the piston 16 has been positioned near the inlet 15. The rod 17 may be attached to the piston 16 either before or after the housing is loaded. The user then positions the collar 18 according to the amount of material that is to be ejected. As noted above, the recessed sides 37 and 38 may be marked to show the relationship between the positioning of the collar 18 on the rod 17 and the amount of material expelled when the plunger is moved into the housing so that stop surfaces 71 and 72 are in contact with one another.

Once the stop collar is adjusted as desired, it is locked in position by the engagement of the projection 58 with a particular one of the grooves 24,25. The cap 14 is then removed and the barrel of the housing 11 is applied as desired. For example, in the case of a medicament, the outlet 13 can be applied to a cavity of the body or some other where the contents are to be expelled. The user wraps his fingers about the portion of the housing 11 near the flange 70, desirably with his thumb and index finger against the flange 70, and forces the rod 17 into the housing 11 by applying pressure to the pommel 19 until the collar 18 has its stop face in engagement with the corresponding stop surface 72 of the flange 70.

It will be noted that the housing 11 can be loaded with a multiple dose of medicament, or a multiple charge of material. In that use the collar 18 is adjusted successively to permit the desired successive dose. Thus the collar is initially positioned away from the pommel 19 and then successively moved towards the pommel according to the successive doses that are required.

In the alternative embodiment of FIG. 5, a housing 50 has an inlet 51 which receives a plunger 53. A piston 52 is shown at the end of the plunger 53 in sealing engagement with the inner walls 54 of the housing 50. The interior of the housing 50 is indicated generally by reference numeral 55. At the distal end of the plunger 53 there is included a pommel 54. It will be noted that the construction of FIG. 5 generally resembles that of FIG. 1 except that a stop collar 56 of different configuration is employed and that the end of the housing beyond the flange (corresponding to that of FIG. 1) includes a concave seat 66 for mating with the collar 56 when the plunger 53 is fully operated.

The particular collar 56 of FIG. 5 is shown in section in FIGS. 6 and 7, the latter showing the collar in the process of being adjusted. As seen in FIG. 6, the collar 56 is annular member that is mounted circumferentially about the plunger 53. The sides 57 and 58 are deformable, and the rod 53 has the same I-beam shape in cross section as before, with the lower part of the collar having a track 60 defined by internal prongs 61 and 62 which embrace the lower beam portion of the rod 53. The top portion of the collar has ratchet members 64 which mesh with grooves 65 of the rod 53. When the sides 57 and 58 are depressed, the ratchet members 64 are lifted from the groove 65 so that the collar can be moved freely along the track 60.

When the rod 53 is moved into the housing the maximum penetration is determined by the collar 56 as shown in FIG. 8.

The connection of the piston 16 to the plunger 17, and similarly of the piston 52 to the plunger 53, is illustrated in FIGS. 9 and 10. As shown specifically for the plunger 17 in FIG. 9, the end of the plunger which is insertable into the housing 11 includes a hub 21 with circular prongs 22 and 35 which are spaced from one another by a shoulder 23. The hub 21 receives the piston 16 as illustrated in FIG. 10. For that purpose, the piston 16 has a hollow central portion with convex walls 46 and exterior concave walls 42. The periphery of the piston 16 forms sealing lips 41. In operation the hub 21 engages the piston 16 and seats in the opening 45 with the convex walls 46 in the interval between the prongs 22 and 35. When the plunger 17 is withdrawn from the housing 11, it is separable from the piston when the latter engages the rim 39.

While various aspects of the invention have been set forth by the drawings and specification, it is to be understood that the foregoing detailed description is for illustration only and that various changes in parts, as well as the substitution of equivalent constituents for those shown and described may be made without departing from the spirit and scope of the invention as set forth in the appended claims.

What is claimed is:

1. A delivery device comprising a housing having an outlet for material to be delivered therefrom: a plunger which can be reciprocated within said housing and means for controlling the extent of reciprocation of said plunger to regulate the amount of material expelled and delivered from said outlet wherein the controlling means is a stop means comprising an ajustably positioned collar surrounding said plunger and located externally of said housing wherein said collar includes compressible side portions to assist in fixing the adjustment position of said collar.

* * * * *